United States Patent [19]

Lee

[11] Patent Number: 4,927,981

[45] Date of Patent: May 22, 1990

[54] MANUFACTURE OF CHLOROFORM

[75] Inventor: Kung H. Lee, Chadds Ford, Pa.

[73] Assignee: E. I. Du Pont de Nemours and Company, Wilmington, Del.

[21] Appl. No.: 257,355

[22] Filed: Oct. 13, 1988

Related U.S. Application Data

[63] Continuation of Ser. No. 119,397, Nov. 10, 1987, abandoned.

[51] Int. Cl.$^5$ .............................................. C07C 17/22
[52] U.S. Cl. .................................................... 570/255
[58] Field of Search ......................................... 570/255

[56] References Cited

U.S. PATENT DOCUMENTS 1,975,727 10/1934 Levine .
3,502,734 3/1970 Baird et al. .

Primary Examiner—Howard T. Mars

[57] ABSTRACT

A process is disclosed for the manufacture of chloroform by partial chlorination of methyl chloride-methylene chloride mixtures to produce a chlorinated product mixture containing chloroform, methyl chloride, methylene chloride and little or no carbon tetrachloride, the amount of methylene chloride being substantially equal to the amount employed in the initial feed mixture and the amount of carbon tetrachloride corresponding to less than 0.1 mole of chloroform in the product.

9 Claims, No Drawings

MANUFACTURE OF CHLOROFORM

This application is a continuation of application Ser. No. 07/119,397 filed Nov. 10, 1987.

BACKGROUND OF THE INVENTION

1. Field of the Invention

This invention relates to the manufacture of chloroform by partial chlorination of methyl chloridemethylene chloride mixtures.

2. Prior Art

The chlorinated methanes (methyl chloride, methylene chloride, chloroform and carbon tetrachloride) are well-known articles of commerce and are generally prepared by chlorination of an underchlorinated raw material. As the demand for the individual members of the series varies from time to time, it is desirable to be able to control their production accordingly.

At present the demand for chloroform is high, that for methylene chloride and carbon tetrachloride is low. The existing chlorination processes, however, are not entirely satisfactory for producing chloroform to the substantial exclusion of the other polychloromethanes. For example, the direct chlorination of methane for this purpose (described in SRI #126, $C_1$ Chlorinated Hydrocarbons, published August 1978, pages 49 to 96) is difficult to control and expensive to operate because of the necessity of recycling large amounts of methane, methyl chloride and methylene chloride. It also tends to produce undesirably high ratios of carbon tetrachloride to chloroform, which constitutes a cost penalty in view of the relatively low demand for the tetrachloride.

The production of methyl chloride is readily controlled by utilizing the reaction of hydrogen chloride with methanol, and for this reason it is an attractive starting material for the higher chlorinated methanes.

Baird, Baumgarten and Gentilucci, U.S. Pat. No. 3,502,734, describe a process of chlorinating methyl chloride and/or methylene chloride for the production of methylene chloride and/or chloroform with minimum formation of by-product carbon tetrachloride. The process involves (a) operating at pressures above the critical pressure of the reaction mixture, (b) preheating the ingredients, in specified proportions, to a specified temperature range to initiate the reaction, and (c) allowing this exothermic chlorination reaction to proceed adiabatically to a higher temperature close to the critical temperature of the reaction mixture, so as to capitalize on the high heat capacity of the mixture at such higher temperatures, until the chlorine reactant is substantially completely consumed. The mol ratio of chlorine to the chlorinated methane feedstock is in the range of 1:3 to 1:12. The mol ratio of methyl chloride to methylene chloride can also vary widely, ranging from 1.2:1 to 1.8:1 in the working examples.

Although the patent shows that more chloroform than methylene chloride can be produced under the disclosed conditions and that both can be obtained to the substantial exclusion of carbon tetrachloride, it is also apparent that the amount of methylene chloride produced is a substantial proportion of the total chlorinated methane production and corresponds to a significant net production of methylene chloride, which is disadvantageous in times of low methylene chloride demand.

SUMMARY OF THE INVENTION

What has been discovered is a process for the manufacture of chloroform by the partial chlorination of methyl chloride and methylene chloride mixtures, which process comprises providing an initial feed mixture consisting essentially of chlorine, methyl chloride, methylene chloride and optionally chloroform and/or hydrogen chloride in amounts such that the mol ratio of chlorine to said chlorinated methanes is in the range of from about 0.15:1 to about 0.21:1, the mol ratio of methyl chloride to methylene chloride is about 1.5:1 and the mol ratio of methylene chloride to chloroform is at least about 6:1;

feeding said mixture at a pressure of about 13 to 130 atmospheres to a reactor that minimizes backmixing of the mixture components and heating said mixture to a temperature in the range of from about 220° to about 500° C. at which reaction of the chlorine with the chloromethanes in the feed mixture is initiated;

maintaining said reaction under said conditions until substantially all the chlorine has reacted;

recovering a chlorinated product mixture containing chloroform, methyl chloride, methylene chloride and little or no carbon tetrachloride, the amount of methylene chloride being substantially equal to the amount employed in the initial feed mixture and the amount of carbon tetrachloride corresponding to less than 0.1 mol of chloroform in the product; and separating chloroform from the product mixture.

DETAILED DESCRIPTION OF THE INVENTION

Reaction temperatures and pressures can vary widely as is well-known in the chlorination art. The temperature should be sufficiently high to initiate the chlorination reaction and allow it to proceed adiabatically. For example, the temperature can range from about 220° to 500° C. and preferably will be at least 250° C. The pressure can range from about 13 to 130 atmospheres and preferably will be at least about 17 atmospheres. More preferably, the pressure will be sufficiently high to maintain the reaction mixture in a super-critical fluidized state, thereby to minimize volumetric expansion of the reaction mixture when the temperature increases adiabatically as the exothermic chlorination proceeds.

Thus, a preferred embodiment of the invention is a continuous process which comprises (1) providing a feed mixture consisting essentially of $Cl_2$, $CH_3Cl$, $CH_2Cl_2$ and optionally $CHCl_3$ and/or HCl in amounts such that the mole ratio of $Cl_2$ to the chlorinatable chlorinated methanes is about 0.21:1, the mol ratio of $CH_3Cl$ to $CH_2Cl_2$ is about 1.5:1 and the mol ratio of $CH_2Cl_2$ to $CHCl_3$ is at least 6:1, (2) continuously feeding the mixture at a pressure of at least 65 atmospheres to a heatable reaction zone, (3) heating the mixture in said zone to a temperature at which the reaction of $Cl_2$ with said chloromethanes is initiated, (4) continuously feeding the heated mixture to an adiabatic pipeline reaction zone under flow conditions that minimize backmixing of the mixture, (5) allowing the chlorination reaction to proceed adiabatically under said flow conditions until substantially all the $Cl_2$ has reacted, then (6) recovering a chlorinated product mixture containing $CHCl_3$, $CH_3Cl$ and little or no $CCl_4$, the amount of $CH_2Cl_2$ being substantially equal to the amount employed in the feed mixture and the amount of $CCl_4$ corresponding to less than 0.1 mol per mol of the $CHCl_3$ product.

The reaction product mixture is separable by conventional methods, conveniently by distillation. The $CH_3Cl$ and $CH_2Cl_2$ fractions, including any unseparated $CHCl_3$, can be recycled along with make-up $CH_3Cl$ to provide a $CH_3Cl$ to $CH_2Cl_2$ mol ratio of about 1.5:1 for further conversion to $CHCl_3$ in accordance with the process of the invention.

Except as modified by the disclosure that follows, the invention process will preferably be conducted as described in U.S. Pat. No. 3,502,734, which description is incorporated herein by reference. As disclosed in the referenced patent, the pressure on the reactants during the course of the chlorination is more preferably in the range of about 85 to 130 atmospheres, which pressures are above the critical pressure of the reaction mass. The reaction temperature will preferably also be above the critical temperature of the feed mixture or at least about 220° C. In a preferred embodiment the initial reaction mixture is fed to a heatable reaction zone, which may be a pipeline reactor, at a pressure above its critical pressure and heated to at least 220° C., preferably to at least 250° C., to initiate the reaction. The temperature during this stage of the reaction can be still higher, for example, around 300° C. The heated reaction mass then passes to an adiabatic reaction zone where chlorination continues with liberation of heat, resulting in a further increase in temperature. The temperature in this stage of the reaction can range from about 300° to about 450° C., and even as high as 500° C. Reaction is continued adiabatically until the chlorine is consumed.

The invention process is designed to provide net production of $CHCl_3$ with substantially no net production of $CH_2Cl_2$ and little or no production of $CCl_4$. The feed mixture mol ratios are critical, particularly the $CH_3Cl$ to $CH_2Cl_2$ mol ratio. It is important to hold this ratio as close to 1.50:1 as is practicable to avoid net production of $CH_2Cl_2$. That the $Cl_2$ to chlorinatable chloromethanes mol ratio is less than stoichiometric means that unreacted $CH_3Cl$ and $CH_2Cl_2$ will appear in the reaction product mixture along with product $CHCl_3$ and by-product HCl. For practical, i.e., economic, operation, it is desirable not only to recycle the unreacted chloromethanes but to minimize the total amount of such recycle material. Thus, although the $Cl_2$ to chloromethanes ratio can be as low as 0.15:1, it is preferred that it not be less than about 0.17:1 and highly preferred that it be held as close to 0.21:1 as is practicable in the initial feed mixture since the smaller this ratio the larger the amount of unreacted $CH_3Cl$ and $CH_2Cl_2$ in the final product mixture. Ratios higher than about 0.21:1 tend to produce excessively high adiabatic reaction temperatures and are to be avoided. On the other hand, the $CH_2Cl_2$ to $CHCl_3$ ratio, which is designed to minimize $CCl_4$ production, should be as high as possible. Although it can be as low as 6:1, it is preferred the $CH_2Cl_2$ to $CHCl_3$ ratio be at least 10:1 and more highly preferred that the $CHCl_3$ be absent altogether from the initial feed mixture. Although HCl can be present in the initial feed mixture to serve as as a heat sink, it may sometimes be preferred that the HCl be substantially absent from the initial mixture. Thus, the ideal initial feed mixture will consist of $Cl_2$, $CH_3Cl$ and $CH_2Cl_2$ in the stated 0.21:1 and 1.50:1 mol ratios.

The term "about" as used herein to define the above mol ratios is meant to include variation of ±15 percent, preferably not more than ±10 percent, from the stated values, provided the sum of the deviation from the $Cl_2$ to chlorinatable chloromethanes ratio and the deviation from the $CH_3Cl$ to $CH_2Cl_2$ ratio is not more than 15%, preferably not more than 10%, regardless of the sign (positive or negative) of the deviation.

By substantially no net production of $CH_2Cl_2$ and $CCl_4$ is meant not more than 0.1 mol of each of these substances per mol of $CHCl_3$ produced. The feed stream mol ratios can be controlled within the defined limits in order to avoid substantial net production of $CH_2Cl_2$ and $CCl_4$.

It will be noted the production of $CHCl_3$ with substantially no net production of $CH_2Cl_2$ and $CCl_4$ depends upon both $CH_3Cl$ and $CH_2Cl_2$ as well as $Cl_2$ in the initial feed mixture. The chlorination process can be visualized as involving the utilization of one molar proportion of $Cl_2$ to produce $CH_2Cl_2$ from $CH_3Cl$ and a second molar proportion to produce $CHCl_3$ from $CH_2Cl_2$. Overall, two mols of $Cl_2$ are required to produce one mol of $CHCl_3$. Therefore, the maximum theoretical efficiency of the process for producing $CHCl_3$ with no net production of $CH_2Cl_2$ and $CCl_4$ is the ratio of the mols of $CHCl_3$ produced to the mols of chlorine consumed in the reaction, or 0.50. Efficiencies less than 0.50 reflect net production of $CH_2Cl_2$ and/or $CCl_4$. The process of the invention can readily provide $CHCl_3$ in high production efficiencies as shown in the Examples.

It is also important for practical operation that the reactor be of the kind that minimizes backflow of the reactants during the chlorination reaction, since the greater the degree of backmixing that occurs the greater will be the amount of unwanted $CCl_4$ produced.

A preferred reactor for carrying out the continuous process of the invention is an unpacked pipeline reactor having a heatable zone and an adiabatic zone and whose overall length is at least 125 times its inside diameter. Rate of flow of the reaction mixture through the line should be high enough, for example, at Reynolds numbers of at least 5000, to minimize backmixing of the reactants. The total reaction time from when the reactants leave the heatable zone of the pipeline reactor to when they leave the adiabatic zone is generally around 0.5 to 3 minutes, most usually 1 to 1.5 minutes depending upon the temperature. The higher the temperature, the shorter the time required.

The reaction is further illustrated in the accompanying Examples. The reaction system involves two pumps—one for $Cl_2$, another for the chloromethanes—a high pressure mixer for mixing the reactants and a pipeline reactor having a separate heatable zone and an adiabatic zone. The pumps are designed and operated to provide the reactants at pressures of at least about 65 atmospheres to the mixing device where the reactants are mixed and fed to the pipeline reactor made of high nickel alloy. The heatable section of the reactor is surrounded by a heating jacket, which serves as the means for heating the reactants to a chlorination temperature. The heatable zone leads to the adiabatic zone of the reactor, which is covered with pipe insulation. At the end of the pipeline reactor is a pressure let-down valve through which the reaction mixture passes for recovery and workup. The workup system includes means for venting and recovering by-product HCl gas and means for the distillation, separation and recovery of $CH_3Cl$, $CH_2Cl_2$, $CHCl_3$ and $CCl_4$.

EXAMPLES 1-3

A reactant feed composition as detailed below is fed at a pressure of 100 atmospheres to the heatable section of the pipeline reactor described above where it is heated to 250° C. to initiate the reaction. The reaction mass reaches a maximum temperature of about 450°–500° C. in the adiabatic section of the reactor. The residence time in the adiabatic section of the reactor is about 1 minute, which is sufficient for the initial charge of $Cl_2$ to be consumed.

The reaction is repeated two times with the feed mixture being varied as summarized in Table A below. Table A also includes the effluent composition and the distribution of products for each run. The sensitivity of the process to slight variations in the $Cl_2$ content and the presence of $CHCl_3$ in the initial feed mixture is shown in Table B.

Tables A and B show that the invention process is capable of producing $CHCl_3$ from controlled $CH_3Cl$-$CH_2Cl_2$-$CHCl_3$ feed compositions to the substantial exclusion of $CH_2Cl_2$ and $CCl_4$ on a net production basis. The data also show that the product distribution is sensitive to the $Cl_2$/chloromethanes ratio and that it is beneficial to exclude $CHCl_3$ altogether from the initial feed composition.

TABLE A

Examples 1 to 3 of the Invention

| | Moles | Wt | Wt % |
|---|---|---|---|
| Example 1 | | | |
| Reactor Feed Compositon | | | |
| $Cl_2$ | 2.24 | 158.8 | 18.7 |
| $CH_3Cl$ | 6.00 | 302.9 | 35.7 |
| $CH_2Cl_2$ | 4.00 | 339.5 | 40.0 |
| $CHCl_3$ | 0.40 | 47.8 | 5.6 |
| $CCl_4$ | — | — | — |
| | 12.64 | 849.0 | 100.0 |
| Reactor Effluent Composition | | | |
| $CH_3Cl$ | 4.92 | 248.4 | 29.3 |
| $CH_2Cl_2$ | 4.00 | 339.6 | 40.0 |
| $CHCl_3$ | 1.40 | 167.1 | 19.7 |
| $CCl_4$ | 0.08 | 12.3 | 1.4 |
| HCl | 2.24 | 81.6 | 9.6 |
| | 12.64 | 849.0 | 100.0 |
| Product | | | |
| $CH_2Cl_2$ | — | — | — |
| $CHCl_3$ | 1.00 | 119.4 | 90.7 |
| $CCl_4$ | 0.08 | 12.3 | 9.3 |
| | 1.08 | 131.7 | 100.0 |
| $CHCl_3/CCl_4$ Wt. Ratio | | 9.7 | |
| Recycle | | | |
| $CH_3Cl$ | 4.92 | 248.4 | |
| $CH_2Cl_2$ | 4.00 | 339.6 | |
| $CHCl_3$ | 0.40 | 47.6 | |
| | 9.32 | 635.6 | |
| By-Product HCl | 2.24 | 81.6 | |
| Example 2 | | | |
| Reactor Feed Compositon | | | |
| $Cl_2$ | 2.12 | 150.3 | 19.0 |
| $CH_3Cl$ | 6.00 | 303.0 | 38.2 |
| $CH_2Cl_2$ | 4.00 | 339.6 | 42.8 |
| $CHCl_3$ | — | — | — |
| $CCl_4$ | — | — | — |
| | 12.12 | 792.9 | 100.0 |
| Reactor Effluent Composition | | | |
| $CH_3Cl$ | 4.96 | 250.4 | 31.6 |
| $CH_2Cl_2$ | 4.00 | 339.6 | 42.8 |
| $CHCl_3$ | 1.00 | 119.4 | 15.1 |
| $CCl_4$ | 0.04 | 6.2 | 0.8 |
| HCl | 2.12 | 77.3 | 9.7 |
| | 12.12 | 792.9 | 100.0 |
| Product | | | |

TABLE A-continued

Examples 1 to 3 of the Invention

| | Moles | Wt | Wt % |
|---|---|---|---|
| $CH_2Cl_2$ | — | — | — |
| $CHCl_3$ | 1.00 | 119.4 | 95.1 |
| $CCl_4$ | 0.04 | 6.2 | 4.9 |
| | 1.04 | 125.6 | 100.0 |
| $CHCl_3/CCl_4$ Wt. Ratio | | 19.3 | |
| Recycle | | | |
| $CH_3Cl$ | 4.96 | 250.4 | |
| $CH_2Cl_2$ | 4.00 | 339.6 | |
| $CHCl_3$ | — | — | |
| | 8.96 | 590.0 | |
| By-Product HCl | 2.12 | 77.3 | |
| Example 3 | | | |
| Reactor Feed Compositon | | | |
| $Cl_2$ | 2.01 | 142.5 | 17.9 |
| $CH_3Cl$ | 6.00 | 302.9 | 38.0 |
| $CH_2Cl_2$ | 4.00 | 339.6 | 42.6 |
| $CHCl_3$ | 0.10 | 11.9 | 1.5 |
| $CCl_4$ | — | — | — |
| | 12.11 | 796.9 | 100.0 |
| Reactor Effluent Composition | | | |
| $CH_3Cl$ | 4.99 | 251.9 | 31.6 |
| $CH_2Cl_2$ | 4.07 | 345.5 | 43.3 |
| $CHCl_3$ | 0.98 | 117.0 | 14.7 |
| $CCl_4$ | 0.06 | 9.2 | 1.2 |
| HCl | 2.01 | 73.3 | 9.2 |
| | 12.11 | 796.9 | 100.0 |
| Product | | | |
| $CH_2Cl_2$ | 0.07 | 5.9 | 4.9 |
| $CHCl_3$ | 0.88 | 105.0 | 87.4 |
| $CCl_4$ | 0.06 | 9.2 | 7.7 |
| | 1.01 | 120.1 | 100.0 |
| $CHCl_3/CCl_4$ Wt. Ratio | | 11.4 | |
| Recycle | | | |
| $CH_3Cl$ | 4.99 | 251.9 | |
| $CH_2Cl_2$ | 4.00 | 339.6 | |
| $CHCl_3$ | 0.10 | 12.0 | |
| | 9.09 | 603.5 | |
| By-Product HCl | 2.01 | 73.3 | |

TABLE B

Selective Preparation of Chloroform

| | Example | | |
|---|---|---|---|
| Initial Feed Composition | 1 | 2 | 3 |
| Mol Ratio | | | |
| $Cl_2/CH_3Cl$, $CH_2Cl_2,CHCl_3$ | 0.215 | 0.21 | 0.199 |
| $CH_3Cl/CH_2Cl_2$ | 1.5 | 1.5 | 1.5 |
| $CH_2Cl_2/CHCl_3$ | 10.0 | * | 40.0 |
| Net Production, Mols | | | |
| $CHCl_3$ | 1.0 | 1.0 | 0.88 |
| $CH_2Cl_2$ | 0 | 0 | 0.07 |
| $CCl_4$ | 0.08 | 0.04 | 0.06 |
| Product Mol Ratio | | | |
| $CHCl_3/CH_2Cl_2$ | * | * | 12.6 |
| $CHCl_3/CCl_4$ | 12.5 | 25.0 | 14.7 |
| Chlorination Efficiency | | | |
| Mols $CHCl_3$ produced per Mol $Cl_2$ consumed | 0.45 | 0.47 | 0.44 |

*infinite

I claim:

1. A process for the manufacture of chloroform by the partial clorination of methyl chloride and methylene chloride mixtures, which process comprises
providing an initial feed mixture consisting essentially of chlorine, methyl chloride and methylene chloride in amounts such that the mol ratio of chlorine to said chlorinated methanes is in the range of from about 0.15:1 to about 0.21:1 and the mol ratio of methyl chloride to methylene chloride is about 1.5:1;

feeding said mixture at a pressure of about 13 to 130 atmospheres to a reactor that minimizes backmixing of the mixture components and heating said mixture to a temperature in the range of from about 220° to about 500° C. at which reaction of the chlorine with the chloromethanes in the feed mixture is initiated;

maintaining said reaction under said conditions until substantially all the chlorine has reacted;

recovering a chlorinated product mixture containing chloroform, methyl chloride, methylene chloride and little or no carbon tetrachloride, the amount of methylene chloride produced being no more than 0.1 mol per mol of chloroform produced and the amount of carbon tetrachloride corresponding to less than 0.1 mol of carbon tetrachloride per mol of chloroform in the product; and separating chloroform from the product mixture.

2. A process as in claim 1 wherein the reactor comprises two zones, a first zone which is a heatable zone and a second zone which is an adiabatic zone, the initial feed mixture being first fed to the heatable zone where it is heated to a temperature of about 220° to about 300° C. to initiate the reaction, then is fed to the adiabatic zone such that there is substantially no backmixing of the reaction mixture where the reaction is allowed to proceed adiabatically to a higher temperature up to about 450° to 500° C. until substantially all the chlorine has reacted.

3. A process as in claim 2 wherein the initial feed mixture is at a pressure of at least about 65 atmospheres and the feed mixture is heated in said heatable zone to a temperature of about 250° to about 300° C.

4. A process as in claim 2 wherein the feed mixture pressure is between about 80 and 110 atmospheres.

5. A process as in any of claims 1 to 4 wherein the mol ratio of chlorine to the chlorinated methanes in the feed mixture is not less than about 0.17:1.

6. The process of claim 5 wherein the mol ratio of chlorine to said chloromethanes is about 0.21:1.

7. The process of claim 1 wherein the process is operated continuously.

8. A process for the manufacture of chloroform by the partial chlorination of methyl chloride and methylene chloride mixtures, which process comprises providing an initial feed mixture consisting essentially of chlorine, methyl chloride, methylene chloride, chloroform and/or hydrogen chloride in amounts such that the mol ratio of chlorine to said chlorinated methanes is in the range of from about 0.15:1 to about 0.21:1, the mol ratio of methyl chloride to methylene chloride is about 1.5:1 and mol ratio of methylene chloride to chloroform is at least about 6:1;

feeding said mixture at a pressure of about 13 to 130 atmospheres to a reactor that minimizes backmixing of the mixture components and heating said mixture to a temperature in the range of from about 220° to about 500° C. at which reaction of the chlorine with the chloromethanes in the feed mixture is initiated;

maintaining said reaction under said conditions until substantially all the chlorine has reacted;

recovering a chlorinated product mixture containing chloroform, methyl chloride, methylene chloride and little or no carbon tetrachloride, the amount of methylene chloride produced being not more than 0.1 mol per mol of chloroform produced and the amount of carbon tetrachloride corresponding to less than 0.1 mol of carbon tetrachloride per mol of chloroform in the product; and separating chloroform from the product mixture.

9. The process of claim 8 wherein the mol ratio of methylene chloride to chloroform in the feed mixture is at least 10:1.

* * * * *